(12) United States Patent
Shiju

(10) Patent No.: US 8,278,487 B2
(45) Date of Patent: Oct. 2, 2012

(54) CATALYTIC PROCESS FOR THE AMMOXIMATION OF CARBONYL COMPOUNDS

(75) Inventor: Nirappurackal Raveendran Shiju, Amsterdam (NL)

(73) Assignee: DSM IP Assets B.V., Amsterdam (NL)

( * ) Notice: Subject to any disclaimer, the term of this patent is extended or adjusted under 35 U.S.C. 154(b) by 256 days.

(21) Appl. No.: 12/700,280

(22) Filed: Feb. 4, 2010

(65) Prior Publication Data

US 2011/0190539 A1    Aug. 4, 2011

(51) Int. Cl.
*C07C 249/04* (2006.01)
*C07C 251/44* (2006.01)

(52) U.S. Cl. .......................... 564/259; 564/253; 564/262

(58) Field of Classification Search .................. 564/253, 564/259, 262

See application file for complete search history.

(56) References Cited

U.S. PATENT DOCUMENTS

| | | | |
|---|---|---|---|
| 3,104,261 A * | 9/1963 | Young | ........................... 564/262 |
| 3,574,750 A | 4/1971 | Yasui et al. | |
| 4,745,221 A | 5/1988 | Roffia et al. | |
| 6,930,204 B2 * | 8/2005 | Ono et al. | ..................... 564/253 |

FOREIGN PATENT DOCUMENTS

| | | |
|---|---|---|
| EP | 0347926 B1 | 11/1994 |
| EP | 1142871 A1 | 12/1999 |
| GB | 1092899 | 2/1966 |
| WO | 9308160 A1 | 4/1993 |

OTHER PUBLICATIONS

Database CAPLUS on STN, Acc. No. 2003:793566, Hagitani, JP 2003286238 A (Oct. 10, 2003) (abstract).*
European Search Report dated Aug. 5, 2010 for 10152633.3-1211.

* cited by examiner

*Primary Examiner* — Brian J Davis
(74) *Attorney, Agent, or Firm* — Westman, Champlin & Kelly; Z. Peter Sawicki

(57) ABSTRACT

The present disclosure pertains to a process for preparing an oxime in which a carbonyl compound is reacted in the liquid phase with $NH_3$ and $H_2O_2$ in the presence of a catalyst to form the corresponding oxime, wherein the catalyst comprises a catalytic component selected from the oxides of metals of group 5 and group 6. The use of a niobia catalyst is particularly preferred. The process according to the disclosure is suitable for the manufacture of numerous oximes, in particular cyclohexanone oxime.

21 Claims, No Drawings

CATALYTIC PROCESS FOR THE AMMOXIMATION OF CARBONYL COMPOUNDS

BACKGROUND

The discussion below is merely provided for general background information and is not intended to be used as an aid in determining the scope of the claimed subject matter.

The present disclosure pertains to a catalytic process for the ammoximation of carbonyl compounds to form oximes using a catalyst.

Oximes, in general, are important chemical intermediates. A particularly important component in this respect is cyclohexanone oxime, which is a precursor for ε-caprolactam, the monomer for nylon-6. Other important oximes include cyclododecanone oxime, salicylaldoxime, and acetophenone oxime.

Processes for ammoximation of carbonyl compounds in the liquid phase using a catalyst are known in the art.

For example, U.S. Pat. No. 4,745,221 describes a catalytic process for preparing cyclohexanone oxime by reacting cyclohexanone with $NH_3$ and $H_2O_2$ in the liquid phase in the presence of a catalyst comprising titanium-silicalite.

EP347926 describes a catalytic process for the manufacture of oximes from carbonyl compounds using as catalyst a solid composition consisting of silicon, titanium, and oxygen, which composition is an amorphous solid. The best results are obtained when the reaction is carried out in t-butanol or cyclohexanol.

There are disadvantages associated with the processes described in these references. In the first place, titanium silicalite is a specialty chemical requiring a specified synthesis route which is complex and difficult. t-Butanol and cyclohexanol are less attractive as solvents from an environmental point of view.

SUMMARY

This Summary and the Abstract herein are provided to introduce a selection of concepts in a simplified form that are further described below in the Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the background.

The present description pertains to a process for preparing an oxime in which a carbonyl compound is reacted in the liquid phase with $NH_3$ and $H_2O_2$ in the presence of a catalyst to form the corresponding oxime, wherein the catalyst comprises a catalytic component selected from the oxides of metals of group 5 and group 6.

DESCRIPTION

This disclosure describes a process for manufacturing oximes from carbonyl compounds which does not suffer from the disadvantages described previously. This disclosure describes a process in which a catalyst is used which requires no complex and difficult synthesis methods or post-treatments, and which shows high activity also in the presence of environmentally attractive solvent like water.

It has been found that the use of a catalyst of this type makes for a process with high selectivity and high activity, resulting in a high yield of oxime. The process avoids by-products obtained in the uncatalyzed process using hydroxylamine. Also, the reaction can be carried out in aqueous media.

The catalyst described in this disclosure comprises a catalytic component selected from the oxides of metals of group 5 and group 6. The catalyst may comprise other catalytic components, viz., oxides of metals of other groups of the periodic table, such as group 4, and group 7-12. However, in a preferred embodiment, the catalytic component consists for at least approximately 50 wt. % of oxides of metals of group 5 and group 6, more in particular for at least approximately 70 wt. %, still more in particular for at least approximately 90 wt. %. In one embodiment, the catalytic component comprises and in another aspect consists essentially of oxides of metals of groups 5 and 6, wherein the wording consists essentially of means that other components are only present at contaminant levels.

Within group 5, the use of vanadium, niobium, or combinations thereof is preferred. The use of niobium is particularly preferred. Within group 6, the use of chromium, molybdenum, and tungsten or combinations thereof is preferred, while the use of tungsten is particularly preferred.

In one embodiment, the catalytic components comprise at least approximately 50 wt. % of group 5 metal components, calculated as oxide, more in particular at least approximately 70 wt. %, still more in particular at least approximately 90 wt. %. In one embodiment, the catalytic component comprises at least approximately 50 wt. % of niobium, calculated as oxide, more in particular at least approximately 70 wt. %, still more in particular at least approximately 90 wt. %. Still more in particular, the catalytic component may consist essentially of group 5 metal components, more in particular, of niobia.

In one embodiment, the catalytic component comprises both niobia and vanadia, in particular at least approximately 50 wt. % of niobium, calculated as oxide, more in particular at least approximately 70 wt. %, still more in particular at least approximately 90 wt. %, and up to approximately 50 wt. %, in particular up to approximately 30 wt. %, more in particular up to approximately 10 wt. % of vanadia.

The catalyst used in the process according to the invention may have the following physical properties:

The surface area (determined via B.E.T) is generally at least approximately 10 $m^2/g$, preferably at least approximately 20 $m^2/g$. In one embodiment, the catalyst has a surface area of at least approximately 80 $m^2/g$. A catalyst with a higher surface area will generally be more active. The upper limit of the surface area is not critical to the present invention. As a general value, an upper limit of approximately 500 $m^2/g$ may be mentioned.

The pore volume (determined via $N_2$ adsorption) is generally at least approximately 0.05 $cm^3/g$, preferably at least approximately 0.10 $cm^3/g$. If the pore volume is too low, the activity of the catalyst may decrease. The upper limit of the pore volume is not critical to the present invention. As a general value, an upper limit of approximately 2 $cm^3/g$ may be mentioned.

The average pore diameter (determined via $N_2$ adsorption) is generally at least approximately 1 nm, preferably at least approximately 2 nm. A range of approximately 3-15 nm may be mentioned as preferred, more in particular approximately 4-10 nm.

The catalyst may be manufactured by processes known in the art. In one embodiment, the catalyst is manufactured by a process in which salts of the relevant metals are subjected to a calcination step in the presence of oxygen, which results in formation of the corresponding oxides. The calcination step generally is carried out at a temperature of approximately 300-900° C., in particular at a temperature of approximately 400-800° C.

In another embodiment, commercially available oxides are used as starting material. They may be used directly, but it may be preferred to subject them to a calcination step, for example to remove contaminants, or to change the catalyst morphology. Suitable calcination conditions include calcination in the presence of air or oxygen or in an inert gas, generally at a temperature of at least approximately 300° C., preferably at least approximately 350° C. As a maximum temperature a value of approximately 900° C. may be mentioned. Preferably, the calcination takes place at a temperature of approximately 350 to 450° C.

Calcination time is generally not critical, and will depend on calcination temperature. A period of approximately 10 minutes to approximately 12 hours is generally suitable; approximately 2-5 hours is more preferable.

The catalytic component may or may not be present on a carrier material. Suitable carrier materials are known in the art and comprise, for example, particles comprising one or more of silica or alumina or activated carbon. If the catalytic component is present on a carrier, it may, for example, be present in an amount of approximately 2-90 wt. %, calculated as oxide, more in particular in an amount of approximately 20-90 wt. %, still more in particular in an amount of approximately 40-90 wt. %. The specific amount will depend on the selected process configuration.

Catalysts containing a carrier material may be manufactured by processes known in the art. A suitable process comprises the steps of combining a precursor for a metal oxide with a carrier material, and calcining the material to convert the precursor into the corresponding oxide. Suitable precursors are for example metal salts. For calcination conditions reference is made to what is stated above. In one embodiment, the step of combining a precursor for a metal oxide with a carrier material comprises contacting particles of a carrier material with an impregnation solution containing metal salts.

In another embodiment, the step of combining a precursor for a metal oxide with a carrier material comprises comulling or otherwise mixing a precursor for a carrier material, e.g., aluminium trihydrate or aluminium monohydrate with a metal oxide, or a precursor for a metal oxide, followed by subjecting the combination to a calcination step to convert the precursor for the carrier material into an oxide. If so desired, a shaping step may be carried out before the precursor for the carrier material is converted into ah oxide, e.g., via extrusion, tabletting, or other means known in the art. It is also possible to process the material in powder form.

The carbonyl compounds used as starting material in the process according to the invention are ketones or aldehydes.

Suitable ketones generally are ketones of the formula R1-CO—R2, wherein R1 and R2 may be the same or different and are selected from alkyl, aryl, cycloalkyl, and heterocyclic aryl groups, optionally substituted with hydroxyl, alkyl, aryl, cycloalkyl, and heterocyclic aryl groups, R1 and R2 having 1-20 carbon atoms, wherein R1 and R2 may be connected to form a cyclic alkyl or (hetero)aryl compound. In one embodiment, preferred ketones are cyclic alkylketones wherein the ring contains 5-12 carbon atoms, and wherein the ring may optionally be substituted with C1-C6 alkyl groups. Particularly preferred ketones are cyclopentanone, cyclohexanone, cycloheptanone, cyclooctanone, t-butyl-cyclohexanone, and cyclododecanone.

In another embodiment preferred ketones are ketones of the formula R1-CO—R2, wherein R1 and R2 are selected from C1-C6 alkyl and phenyl. Examples of suitable ketones within this group include acetone, methyl-ethyl-ketone, acetophenone, and benzophenone.

Suitable aldehydes generally are aldehydes of the formula R3-CHO, wherein R3 is selected from alkyl, aryl, cycloalkyl, and heterocyclic aryl groups, optionally substituted with hydroxyl, alkyl, aryl, cycloalkyl, and heterocyclic aryl groups, R3 having 1-20 carbon atoms. In a preferred embodiment, R3 is selected from optionally substituted phenyl and C1-C10 alkyl. As preferred aldehydes may be mentioned benzaldehyde, p-tolualdehyde, and salycylaldehyde.

Preferred oximes that may be manufactured using the process according to the invention are the oximes corresponding to the preferred ketones and aldehydes mentioned above. As particularly preferred oximes the following compounds may be mentioned cyclohexanone oxime, cyclododecanone oxime, salicylaldoxime, and acetophenone oxime, with cyclohexanone oxime being particularly preferred.

The reaction takes place in the liquid phase. This means that at least the carbonyl compound is in the liquid phase during the reaction.

The reaction is generally carried out in the presence of a liquid medium. The liquid medium helps to ensure good contact between the various reactants, for example by providing a solvent for the $H_2O_2$ and $NH_3$. The liquid medium may also help to prevent the formation of by-products by diluting the reactants.

The liquid medium may be selected from water, organic liquids, and mixtures thereof. Water is the most suitable reaction medium. Organic liquids can also be used, provided that $NH_3$ or, where applicable aqueous ammonia can dissolve therein. The boiling point of the reaction medium should be higher than the preferred reaction temperature.

The use of a liquid medium comprising water is preferred for environmental reasons. Particularly preferred is the use of a medium comprising at least approximately 50 wt. % of water, preferably at least approximately 70 wt. % of water, more preferably at least approximately 90 wt. % of water.

The reaction is carried out at a temperature which is selected such that the carbonyl compound and the reaction medium are present in the liquid phase. The upper limit is governed by the boiling point of these compounds under reaction conditions. The use of a higher reaction temperature leads to an increased reaction velocity, but also to increased formation of by products. The use of a lower reaction temperature leads to an increased selectivity, but also to a decreased reaction velocity. In one embodiment, the reaction is carried out at a temperature of at most approximately 100° C., in particular at most approximately 90° C., more in particular at most approximately 80° C.

In one embodiment, the reaction is carried out at a temperature of at least approximately 4° C., in particular at least approximately 20° C., more in particular at least approximately 50° C.

The reaction preferably is carried out at atmospheric pressure. A pressure of up to approximately 5 bar may be applied to help to increase the concentration of $NH_3$ in the reaction medium.

The molar ratio between carbonyl compound and $NH_3$ generally is in the range of approximately 1:5 to 5:1, in particular in the range of approximately 1:2 to 2:1, more in particular in the range of approximately 1:1 to 1:2. The molar ratio between $NH_3$ and $H_2O_2$ is generally in the range of approximately 1:5 to 5:1, preferably in the range of approximately 1:2 to 2:1. It may be preferred for the ratio between $NH_3$ and $H_2O_2$ to be at least approximately 1:1, more preferably at least approximately 1.5:1, to prevent the occurrence of undesirable side reactions.

It is within the scope of the person skilled in the art to select an appropriate reaction configuration. The process can be carried out in batch mode or in a continuous mode.

Where the process is a batch process, it is preferred to use approximately 0.1-100 parts per weight of catalytic component (calculated as oxide), in particular approximately 1-20 parts per weight, per approximately 100 parts of carbonyl compound. Where the process is a continuous process, the liquid hourly space velocity of the carbonyl compound preferably is in the range of approximately 0.1-100 kg of carbonyl compound per kg of catalytic component (calculated as oxide). Expressed in moles, the carbonyl compound/catalyst molar ratio preferably is approximately 50:1 to 2:1.

The catalyst may be in the form of a fixed bed, e.g., a trickle bed, an ebullated bed or fluid bed, or finely divided in the reaction medium. The size and shape of the catalyst particle will be selected such that it is suitable for use in the selected process. For fixed bed, this generally means a particle diameter in the range of approximately 0.1-15 mm. For a catalyst finely divided in the reaction medium this generally means a diameter of approximately 1 to 1000, preferably approximately 1-100 microns. A process wherein the catalyst is finely divided in the reaction medium may be preferred. It is within the scope of the skilled person to select an appropriate process configuration.

This disclosure will be elucidated by the following Examples, without being limited thereto or thereby.

EXAMPLES

The experiments were carried out as follows:

1 gram of catalyst was brought into a reaction vessel with a volume of 100 ml. The catalyst was suspended in 25 ml of a reaction medium. The reaction medium was kept at a temperature of 78° C. 2 g of carbonyl compound was charged and the whole was stirred continuously with a magnetic stirrer. 2.8 g of a 25% aqueous solution of ammonia was added. 4.6 g of a 30% aqueous solution of $H_2O_2$ was added to the reactor using a syringe pump at a rate of 2 g/h. The stirring continued after the completion of addition so that the total reaction period is three hours. The heating was turned off and the reactor contents were cooled at the end of the reaction. The products were analysed by gas chromatography.

Example 1

Ammoximation of Cyclohexanone—Influence of Catalyst Calcination Temperature

Cyclohexanone was subjected to an ammoximation process as described above. The reaction medium was ethanol. The molar ratio of cyclohexanone:$NH_3$:$H_2O_2$ was 1:2:2. The molar ratio of cyclohexanone:$Nb_2O_5$ was 5:1.

The catalyst was commercially available niobia which was subjected to calcination at different temperatures.

The starting material was niobia ($Nb_2O_5$) with a surface area of 123 m$^2$/g, a pore volume of 0.19 cm$^3$/g, and a an average pore diameter of 5.2 nm.

The starting material was subjected to calcination in air for a period of 4 h, at different temperatures. Calcination temperatures and some catalyst properties are given in table 1A.

TABLE 1A

| Experiment | Calcination temperature (° C.) | surface area (m$^2$/g) | pore volume (cm$^3$/g) | average pore diameter (nm) |
|---|---|---|---|---|
| 1.A | 100 | 122.6 | 0.19 | 5.2 |
| 1.B | 300 | 105.3 | 0.17 | 6.3 |
| 1.C | 400 | 104.7 | 0.15 | 5.8 |
| 1.D | 500 | 59.4 | 0.16 | 8.2 |

The results are presented in Table 1B.

TABLE 1B

| Experiment | Calcination temperature (° C.) | cyclohexanone conversion (%) | selectivity to cyclohexanone oxime (%) |
|---|---|---|---|
| 1.A | 100 | 64.7 | 93.3 |
| 1.B | 300 | 80.3 | 95.2 |
| 1.C | 400 | 97.2 | 95.8 |
| 1.D | 500 | 39.0 | 91.6 |

Example 2

Ammoximation of Various Carbonyl Compounds

An ammoximation process was carried out as described above, using different types of carbonyl compounds. The catalyst was niobia calcined at a temperature of 400° C. as described above. The reaction medium was ethanol. The molar ratio of cyclohexanone:$NH_3$:$H_2O_2$ was 1:2:2. The molar ratio of cyclohexanone:$Nb_2O_5$ was 5:1. The results are presented in Table 2.

TABLE 2

| Experiment | carbonyl compound | conversion (%) | selectivity to oxime (%) |
|---|---|---|---|
| 2.A | cyctooctanone | 77.7 | 99.0 |
| 2.B | cycloheptanone | 30.2 | 99.0 |
| 2.C | cyclohexanone | 97.2 | 95.8 |
| 2.D | cyclopentanone | 36.0 | 97.1 |
| 2.E | benzaldehyde | 48.5 | 99.0 |

Example 3

Ammoximation of Cyclohexanone Using Various Reaction Media

An ammoximation process of cyclohexanone was carried out as described above, using different types reaction media. The catalyst was niobia calcined at a temperature of 300° C. (in experiment 3.A) or 400° C. (in experiments 3.B and 3.C) as described above. The molar ratio of cyclohexanone:$NH_3$:$H_2O_2$ was 1:2:2. The molar ratio of cyclohexanone:$Nb_2O_5$ was 5:1. The results are presented in Table 3.

TABLE 3

| Experiment | reaction medium | cyclohexanone conversion (%) | selectivity to cyclohexanone oxime (%) |
|---|---|---|---|
| 3.A | $CH_3CN$ | 69.3 | 86.0 |
| 3.B | ethanol | 97.2 | 95.8 |
| 3.C | $H_2O$ | 92.0 | 99.0 |

Although the present invention has been described with reference to preferred embodiments, workers skilled in the art will recognize that changes may be made in form and detail without departing from the spirit and scope of the invention.

What is claimed is:

1. A process for preparing an oxime in which a carbonyl compound is reacted in the liquid phase with $NH_3$ and $H_2O_2$ in the presence of a catalyst to form the corresponding oxime, wherein the catalyst comprises a catalytic component selected from the oxides of metals of group 5 and group 6.

2. The process according to claim 1, wherein the catalytic component comprises at least approximately 50 wt. % of oxides of metals of group 5 and group 6.

3. The process according to claim 1, wherein the catalytic component comprises at least approximately 50 wt. % of niobium, calculated as oxide.

4. The process according to claim 3, wherein the catalytic component consists essentially of niobia.

5. The process according to claim 1, wherein the catalyst has a surface area of at least approximately 80 m$^2$/g, a pore volume of at least approximately 0.1 cm$^3$/g, and an average pore diameter of approximately 3-10 nm.

6. The process according to claim 1, wherein the carbonyl compound is a ketone of the formula R1-CO-R2, wherein R1 and R2 may be the same or different and are selected from alkyl, aryl, cycloalkyl, and heterocyclic aryl groups, optionally substituted with hydroxy, alkyl, aryl, cycloalkyl, and heterocyclic aryl groups, R1 and R2 having 1-20 carbon atoms, wherein R1 and R2 may be connected to form a cyclic alkyl or (hetero)aryl compound.

7. The process according to claim 6, wherein the ketone is a cyclic alkylketone wherein the ring contains 5-10 carbon atoms, and wherein the ring may optionally be substituted with C1-C6 alkyl groups.

8. The process according to claim 6, wherein the ketone is a ketone of the formula R1-CO-R2, wherein R1 and R2 are selected from C1-C6 alkyl and phenyl.

9. The process according to claim 1, wherein the carbonyl compound is an aldehyde of the formula R3-CHO, wherein R3 is selected from alkyl, aryl, cycloalkyl, and heterocyclic aryl groups, optionally substituted with hydroxy, alkyl, aryl, cycloalkyl, and heterocyclic aryl groups, R3 having 1-20 carbon atoms.

10. The process according to claim 9, wherein R3 is selected from optionally substituted phenyl and C1-C10 alkyl.

11. The process according to claim 1, wherein the reaction is carried out in the presence of a liquid medium.

12. The process according to claim 1, wherein the reaction is carried out at a temperature of at most approximately 100° C., the temperature being at least approximately 4° C.

13. The process according to claim 1, wherein the molar ratio between carbonyl compound and $NH_3$ is in the range of approximately 1:5 to 5:1, and the molar ratio between $NH_3$ and $H_2O_2$ is in the range of approximately 1:5 to 5:1.

14. The process according to claim 1, wherein where the process is a batch process, and is carried out using approximately 0.1-100 parts per weight of catalytic component (calculated as oxide) per weight per approximately 100 parts of carbonyl compound.

15. The process according to claim 1 wherein the process is a continuous process).

16. The process according to claim 2, wherein the catalytic component comprises at least approximately 50 wt. % of niobium, calculated as oxide.

17. The process according to claim 16, wherein the catalytic component consists essentially of niobia.

18. The process according to claim 6, wherein the ketone is selected from the group consisting of cyclopentanone, cyclohexanone, cycloheptanone, cyclooctanone, t-butyl-cyclohexanone, and cyclododecanone.

19. The process according to claim 6, wherein the ketone is selected from the group consisting of acetone, methyl-ethyl-ketone, acetophenone, and benzophenone.

20. The process according to claim 11 wherein the medium comprises at least 50 wt. % of water.

21. The process according to claim 15, wherein the liquid hourly space velocity of the carbonyl compound is in the range of approximately 0.1-100 kg of carbonyl compound per kg of catalytic component (calculated as oxide).

* * * * *

UNITED STATES PATENT AND TRADEMARK OFFICE
CERTIFICATE OF CORRECTION

PATENT NO. : 8,278,487 B2
APPLICATION NO. : 12/700280
DATED : October 2, 2012
INVENTOR(S) : Nirappurackal Raveendran Shiju It is certified that error appears in the above-identified patent and that said Letters Patent is hereby corrected as shown below:

Claim 15, Column 2, Line 19: please remove -- ) --

Signed and Sealed this
First Day of January, 2013

David J. Kappos
*Director of the United States Patent and Trademark Office*